United States Patent [19]
Nag et al.

[11] Patent Number: 5,869,296
[45] Date of Patent: Feb. 9, 1999

[54] DNA TRANSPOSON TN5SEQ1

[75] Inventors: Dilip K. Nag, Carrboro, N.C.; Henry V. Huang, University City; Douglas E. Berg, St. Louis, both of Mo.

[73] Assignee: Washington University, St. Louis, Mo.

[21] Appl. No.: 4,406

[22] Filed: Jan. 14, 1993

Related U.S. Application Data

[60] Continuation of Ser. No. 508,382, Apr. 12, 1990, abandoned, which is a division of Ser. No. 105,422, Oct. 5, 1987, Pat. No. 5,137,829.

[51] Int. Cl.$^6$ .......................... C12P 19/34; C12N 15/64; C12N 15/70
[52] U.S. Cl. .................. 435/91.3; 435/91.41; 435/172.3
[58] Field of Search .............................. 435/69.1, 172.3, 435/320.1, 91.3, 91.41; 536/24.1

[56] References Cited

U.S. PATENT DOCUMENTS

| | | | |
|---|---|---|---|
| 4,683,202 | 7/1987 | Mullis | 435/91 |
| 4,716,105 | 12/1987 | Mizuuchi et al. | 435/5 |
| 4,766,072 | 8/1988 | Jendrisak et al. | 435/91 |
| 5,137,829 | 8/1992 | Nag et al. | 435/320.1 |

OTHER PUBLICATIONS

Ubben et al, Gene, 53 : pp. 127–134 (1987).
Sasakawa et al, Proc. Natl. Acad. Sci. 80 : 7293–7297 (1983).
Blazey et al.,Proc. Natl. Acad. Sci. 79 : 5011–5015 (1982).
Ciampi et al.,Proc. Natl. Acad. Sci. 79 : 5016–5020 (1982).
Berg et al., Genetics 105, 813–828 (1983).
Berg and Berg, Bio/Technology 1, 417–435 (1983).
Berg and Berg, in Neidhardt et al., *E. coli* and *S. typhimurium*: Cellular and Mol. Biol., 1071–1109 (1987).
Johnson and Reznikoff, Nature 304, 280–282 (1983).
Sasakawa et al., Proc. Natl. Acad. Sci. USA 80, 7293–7297 (1983).
Auserwald et al., Cold Spring Harbor Symp. Quant. Biol. 45, 107–113 (1983).
Krebs and Reznikoff, J. Mol. Biol. 192, 781–791 (1986).
Melton et al., Nucl. Acids. Res. 12, 7035–7056 (1984).
Studier and Moffatt, J. Mol. Biol. 189, 113–130 (1986).
Egelhoff et al., DNA 4, 241–248 (1985).
Nag et al, Gene 64, 135–145 (1988).

*Primary Examiner*—David Guzo
*Attorney, Agent, or Firm*—Scott J. Meyer

[57] ABSTRACT

A novel transposon useful for sequencing long DNAs is disclosed which comprises a partial sequence of transposon Tn5 with the oligonucleotide primers from phages SP6 and T7 inserted near the opposite ends, respectively, of said transposon Tn5.

2 Claims, 11 Drawing Sheets

```
            5    10   15   20   25   30   35   40   45   50   55   60   65   70   75   80   85   90   95   100
            |----0 end----|-------|  T7 RNA                                                                  |
                                  BamHI
CTGACTCTTATACACAAGTAGTAGTAGTCCCTATAGTGAGTCGTATTAGATCCGAGCTTCACGCTGCCGCAAGCACTCAGGGCGCAAGGGCTGCTAAAGGAAG CGGAACACGTAGAAAAGCCAGTCCGCAGAAACGGTGCTGACCCCGGATGAATGTCAGCTACTGGGCTATCTGGACAAGGGAAAAACGCAAGCGCAAAGAGAA AGCAGGTAGCTTGCAGTGGGCTTACATGGCGATAGCTAGAGATGGGCGGTTTTATGGACAGCAAGCGAACCGGAATTGCCAGCTGGGGGCCCTCTGGTAA GGTTGGGGAAGCCCTGCAAAGTAAACTGGATTGCACGGCGGTTCTCCGGCCAAGGATCTGATGGGCCAGGGGATCTATTCGGGTGGAGAGGCTATTCGGCTGCT
                                                                                                        BclI
TTTCGCATGATTGAACAAGATGATTGCACGCAGGTTCTCCGGCCGGTTCTTTTTGTCAAGACCGACCTGTCCGGTGCCCTGAATGAACTGCAGGACGAGGCAGC
    kan →
CTGATGCGGCCGTGTTCCGGCTGTCAGCGCAGGGGCGCCCGGTTCAGCGCAGGGGGGTTCCTTGCGCAGCTGTCGCTGTCGCTCGACGTTGTCACTGAAGCGGGAAGGGACTGGCTGCTATTGGGCGAAGTGCCG GCGGCTATCGTGGCTGGCCACGACGGGGTTCCTTGCCAGCTGTCGCTGTCTCGACGTTGTCACTGAAGCGGGAAGGGACTGGCTGCTATTGGGCGAAGTGCCG
```

FIG.4A

```
GGGCAGGATCTCCTGTCATCTCACCTTGCTCCTGCCGAGAAAGTATCCATCATGGCTGATGCAATGCGGCGGCTGCATACGCTTGATCCGGCTACCTGCC
CATTCGACCACCAAGCGAAACATCGCATCGAGCGAGCACGTACTCGGATGGAAGCCGGTCTCTTGTCGATCAGGATGATCTGGACGAAGAGCATCAGGGCT
                                                                      NcoI
CGGGCCAGCCGAACTGTTCGCCAGGCTCAAGGCGCGCATGGGCCGAGGATCTCGTCGTGACCCATGGCGATGCCTGCTTGCCGAATATCATGGTG
                    BssHI  SphI                            AvaII
GAAAATGGCCGCTTTTCTGGATTCATCGACTGTGGCCGGCTGGGTGTGGCGGACCGGCTATCAGGACATAGGCGTTGGCTACCCGTGATATTGCTGAAGAGC
                                                                                              term.of kan
TTGGCGGCGAATGGGCTGACCGCTTCCTGTCGCTTACGGTATCGCCGCTCCCGATTCGCAGCGCATCGCCTTCTATCGCCTTCTTGACGAGTTCTTCTG
AGCGGGACTCTGGGGTTCGAAATGACCGACCAAGCGACGCCCAACCTGCCATCACGAGATTTCGATTCCACCGCCGCCTTCTATGAAAGGTTGGGCTTCG
        AsuII                                                                              SmaI
GAATCGTTTTCCGGGACGCCGGCTGGATGATCCTCCAGCGCGGGGATCTCATGCTGGAGTTCTTCGCCCACCCCGGGCTCGATCCCCTCGGCGAGTTGGTT
                                                                                              NruI
CAGCAGTTCGGGAAACTCCTGAGCCAACTTGACTGTTTGCATGGCCAGCCTTTCTGATCGCCTCGGGAGAAACGTTGGGATTGCGGTAAATCGGTAA
```

FIG.4B

```
CCGAACTGCAGGAGTGGGGAGGCACGATGGCCGCTTTGGTCGACGATCAGATCTTGATCCCCTGCCGCCATCAGATCCTTGGGGCAAGAAAGCCATCC
                                          ‾‾‾‾‾ ‾‾‾‾‾‾‾‾‾‾
                                           SalI  term. of tnp AGTTTACTTTGCAGGGCTTCCCAACCTTCCCAGAGGGCGCCCCAGCTGGCAATTCCGGTTCGCTTGCTGTCCATAAAACGCCCAGTCTAGTATCGCCA TGTAAGCCACTGCAAGCTACCTGCTTTCTCTTTGCGCTTGCTTTCCCTTGTCCAGATAGCCAGTAGCTGACATTCATCCGGGGTCAGCACCGTTTC TGCGGGACTGGCTTTCTACGTGTTCCGCTTCCTTTAGCAGCCCTTGCGCCCTGAGTGCTTGCGGGCAGCGTGAAGCTTTCTGAGCTGTAACAGCCTGACC
                                                                       ‾‾‾‾‾‾
                                                                       HindIII GCAACAAAACGAGAGGATCGAGACCATCCGCTCCAGATTATCCGGCTCCTCCATGGTTGCCTCTCCGGTCCGCCGGTCCAGCAACAACCATTCAACGGGGT CCTCGATCCGCCAGGCGATGGGTATAAATGTCGATGACCGGCTAGGACTCGACCGGTTGGGCGTTGAGCGTGATATTCCCCTGTTTAGCGGTGATGCCGCCACTGCCCAGGCTCAAGCTCGCC
                                                                   ‾‾‾‾‾
                                                                   NheI CTCACCCTTGGGCGGGTTAATCTCCTCGGCGTTGATTTTTACGGTTATCCACCACGCGGTTATCCGGGAATGCTGATCTGATAGCCACCCAACTCCGGTTGGTTCTTCAGAT
                                                                                      ‾‾‾‾
                                                                                      BsnI GGTCGATCAGATACAACCCAGACTCTACGTCCTTGCGTGGGTGCTTGGAGGCACCACGAAGGCTCGTTATGGCGCCAGCCTGTCCTGCAGATAAGCATG
                                                           ‾‾‾‾‾‾‾
                                                           Eco47III
```

FIG.4C

```
AATATCGGCTTCGCGGTCACAGACCGCAATCACGTTGCTCATCATGCTGCCATGCTGGGCCGTGCCAGCCATTTGCCACTCTCC
TTTCATCCGCATCGGCAGGGTCATCCGGGCATCCACCACTCCTGATGCAGTAATCCTACGGTGCGAATGTGGTGGCCTCGAGCAAGAGAACGGAGT
                                                                       Not I                Xho I
GAACCCACCATCCGCGGGATTTATCCTGAATAGAGCCCAGCTTGCCAAGCTCTTCGGGACCTGGTGGCGATAACTCAAAGAGGTGGTGTCCTCAATGGC
                SacII
CAGCAGTTGCGGAAACTCCTGAGCCAACTTGACTGTTTGCATGGGCGCCAGCCTTTCTGATCGCCTCGGCAGAAACGTTGGGATTGCGGTAAAATCGGTAA
GCGGCCTTCCTGACATGGCTTCACTACCCTCTGATGAGATGGTTATTGATTTACCAGAATATTTGCCAATTGGGCGGGACGTTAACCAAGCGGGCAGTAC
                                                         Ssp I                                    Hpa I
GGGGAGGATCACCCAGGCGCCGGAAGAGAACACAGATTTAGCCCAGTCGGCCGATGAAGAGCAGAAGTTATCATGAACGTTACCATGTTAGGAGG
                                                                                      tnp
TCACATGGAAGTCAGATCCTGGAAAACGGGAAAGGTTCCGTTCAGGACGCTACTTGCGGGATCACATATGTCGTTAGAACGGGCTACAATTAATACAT
                                        SP6 RNA
AACCTTATGTATCATACACATACGATTTAGGTGACACTATAGGATCCCGTACTTGTGTATAAGAGTCAG
                                                                         0 end
                                          BamHI
```

FIG. 4D

DNA TRANSPOSON TN5SEQ1

This is a CONTINUATION of application Ser. No. 07/508,382, filed Apr. 12, 1990 now abandoned, which is a Division of application Ser. No. 07/105,422, filed Oct. 5, 1987, now U.S. Pat. No. 5,137,829.

This invention was made with Government support under Grant No. 37138 awarded by the National Institutes of Health. The Government has certain rights in the invention.

BACKGROUND OF THE INVENTION

This invention relates to a DNA segment or vector system useful for sequencing long deoxyribonucleic acid (DNA) molecules and, more particularly, to a novel prokaryotic transposon.

It is known that certain complex DNA segments, known as transposons, are able to insert into many sites in the genome of their host organisms. That is, certain large segments of DNA called insertion sequences (ISs) when present in closely spaced pairs can move as a unit, carrying along the genes lying between them. These complex units constitute the transposon. They exist in prokaryotes, such as bacteria, as well as in eukaryotes.

Recently, a useful bacterial transposon referred to a Tn5 was discovered and characterized. It is a discrete 5.8 kilobase (kb) segment of bacterial DNA which can insert at high frequency into numerous sites in the chromosomes, plasmids, and temperate phages of gram negative bacteria. It encodes resistance to the aminoglycoside antibiotics kanamycin and neomycin in bacteria, and G418 (genticin) in eukaryotic cells. The restriction enzyme map of Tn5 is illustrated by Berg et al., *Genetics* 105, 813–828, (1983). Further background information on Tn5 can be had by reference to the recent review articles by Berg and Berg, *Bio/Technology* 1, 417–435 (1983); and Berg and Berg in Neidhardt et al., (eds.), *"Escherichia coli* and *Salmonella typhimurium*: Cellular and Molecular Biology," ASM, Washington, D. C., Ch. 63, pp. 1071–1109 (1987).

Two widely used methods for DNA sequence analysis are the base-specific chemical cleavage method [Maxam and Gilbert, *Methods Enzymol.* 65, 499–560 (1980)] and the enzymatic chain termination method [Sanger et al., *Proc. Natl. Acad. Sci. USA* 74, 5463–5467 (1977)]. The chemical cleavage method usually requires knowledge of at least part of the restriction map of the DNA segment to be sequenced, it involves the handling of toxic chemicals, and is relatively time-consuming. The enzymatic chain termination method by comparison is easier, and for many applications has become the method of choice. Generally in this method the DNA segment of interest is cloned in an appropriate vector, and a short oligonucleotide complementary to sequences adjacent to the cloning site is used to prime DNA synthesis in the presence of base-specific DNA chain terminators. Typically, only a few hundred base pairs (bp) can be sequenced from the primer site, and thus a number of strategies have been devised to bring more distant regions near to the primer site. These include subcloning of small DNA fragments, isolation of nested sets of deletion derivatives either in vivo [Ahmed, *Gene* 39, 305–309 (1985)] or in vitro [Sanger et al., *J. Mol. Biol.* 143, 161–178 (1980); Barnes et al., *Methods Enzymol.* 65, 98–122 (1980); Deininger, *Anal. Biochem.* 135, 247–263 (1983); and Messing, *Methods Enzymol.* 101, 20–77 (1983)]; or making new oligonucleotide primers complementary to the end of each sequenced segment [Winnoto et al., *Nature* 324, 679–681 (1986)].

Because the foregoing sequencing methods are laborious, an improved method and vector for the sequencing of long DNAs would have significant use in molecular genetic analysis.

BRIEF DESCRIPTION OF THE INVENTION

In accordance with the present invention a novel prokaryotic transposon and method for the sequencing of long DNAs is provided. This novel vector system is a derivative of transposon Tn5. It consists of a transposable DNA unit comprising at each terminus a segment of 19 nucleotides selected from the group consisting of the O-end and I-end sequences of the Tn5 transposon, restriction enzyme sites positioned less than about 20 nucleotides distant from each said terminal segment, segments of at least 17 nucleotides which are foreign to any Tn5 or native *E. coli* sequence and positioned directly adjacent to each said restriction enzyme site, a Tn5 transposase gene insert and a selectable gene marker for said transposable DNA unit.

It should be understood that the DNA used in the novel transposon of this invention is double-stranded. Due to the complementary nature of DNA base-pairing, the nucleotide sequence of one strand of a double-stranded DNA molecule is sufficient to determine the sequence of the opposing strand.

The 19 base pair long terminal sequences of the novel transposon, the O-end and I-end, are well-known and defined as follows:

O-end sequence

5' CTGACTCTTATACACAAGT
3' GACTGAGAATATGTGTTCA

See, e.g., Berg and Berg, *Bio/Technology* 1, 417–435 (1983); Johnson and Reznikoff, *Nature* 304, 280–282 (1983); and Sasakawa et al., *Proc. Natl. Acad. Sci. USA* 80, 7293–7297 (1983).

I-end sequence

5' CTGTCTCTTGATCAGATCT
3' GACAGAGAACTAGTCTAGA

See Sasakawa et al., Ibid.

Restriction enzyme sites should be located near each of said termini. They can be directly adjacent to (flush) or within about 20 nucleotides distant from the terminal segments. They generally should be the same at each end and are illustrated, for example, by the BamHI sites 5' GGATCC. Additional restriction enzyme sites can be inserted in the transposon as may be desired for particular applications. Any of the common restriction endonucleases can be employed for these purposes.

The foreign nucleotide sequences directly adjacent to the restriction enzyme sites nearest each terminus can be any desired nucleotide sequence which is a 17 bp or larger DNA segment that is foreign to the Tn5 transposon or *E. coli* or other host in which it is desired to insert the transposon of this invention. In a preferred embodiment, referred to herein as Tn5seq1, these foreign sequences contain promoters from phages T7 and SP6, positioned near the left and right ends, respectively, of the transposon. These promoters are commercially available and their nucleotide sequences are well-known.

In the preferred embodiment of the invention, the T7 and SP6 nucleotide sequences act as portable primer binding sites for bidirectional sequencing from the site of insertion. The transcription start sites for the T7 and SP6 RNA polymerases are only 20 and 30 bp away from the ends of the Tn5seq1 transposable DNA unit.

The Tn5 transposase gene used in the transposon of the invention also is well-known. It is described by Auserwald et al., *Cold Spring Harbor Symp. Quant. Biol.* 45, 107–113 (1981), and Krebs and Reznikoff, *J. Mol. Biol.* 192, 781–791 (1986). The transposase gene can be anchored anywhere within the novel vector system of this invention, that is, either within or outside the transposon. In the preferred embodiment, Tn5seq1, the transposase gene is inserted within the transposon.

A selectable gene marker for the transposon must be located within that unit. These markers can be, for example, antibiotic resistant genes such as those conferring resistance to ampicillin, chloramphenicol, kanamycin, tetracycline and the like antibiotics, or a suppressor tRNA gene such as supF of *E. coli*.

The transposon of this invention can be carried in a DNA cloning vector such as a plasmid or phage for delivery of the unit to another DNA molecule or cell. As such, the novel transposon has wide uses, including various types of DNA sequencing in which the unit serves as a source of sites from which to carry out the DNA sequencing.

In particular, the Tn5seq1 of this invention transposes efficiently in vivo into phage, plasmid, and chromosomal target DNAs. It can be used for the sequencing of bacterial genomic DNAs without recombinant DNA cloning, and also of DNAs cloned in phages and multicopy plasmids. Its potential uses also include sequencing by the chemical cleavage method; RNA sequencing with SP6 and T7 RNA polymerases in presence of 3' deoxynucleotides; making RNA transcripts in vitro; and hyperexpression or specific transcription of adjacent genes in vivo (adjacent to the SP6 or T7 ends).

Thus, the Tn5seq1 vector system of this invention is useful in the generation of mutants and/or the rapid screening of DNA sequences. For example, this system can facilitate the sequencing of large pieces of DNA such as those cloned in U.S. application Ser. No. 38,280, filed Apr. 15, 1987, and assigned to a common assignee. Also, the system can be used to generate random insertions in bacterial (e.g., Pseudomonas) chromosomes which can then be screened at the organism level for desirable functions. The defined Tn5seq1 vector can facilitate identification and sequencing of the mutated function. Other target organisms are, for example, Bordetella, Yersinia and *Myxococcus xanthus*.

The Tn5seq1 is conveniently constructed in a pBR322 derived plasmid. Plasmid pBR322 is a well characterized, commercially available cloning vector having a molecular weight of $2.6 \times 10^6$. It is the workhorse of molecular biology, recently reviewed by Balbas et al., *Gene* 50, 3–40 (1987), and its sequence and restriction enzyme map has been published by Maniatis et al., *Molecular Cloning:A Laboratory Manual*, Cold Spring Harbor Laboratory, Cold Spring Harbor, N.Y. (1982). An amended sequence is described by Peden, *Gene* 22, 277–280 (1983).

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention in conjunction with the appended drawings, in which briefly:

FIG. 1 is a diagrammatic representation which shows the structure of the transposon Tn5seq1 in a preferred embodiment of the invention.

FIG. 2, split into two parts, FIGS. 2A and 2B, is a diagrammatic representation which shows the construction of the Tn5seq1 containing plasmid pBRG1408.

FIG. 4 (parts A–D) shows the complete nucleotide sequence of Tn5seq1 split into four parts, FIGS. 4A, 4B, 4C and 4D.

Figure 1:
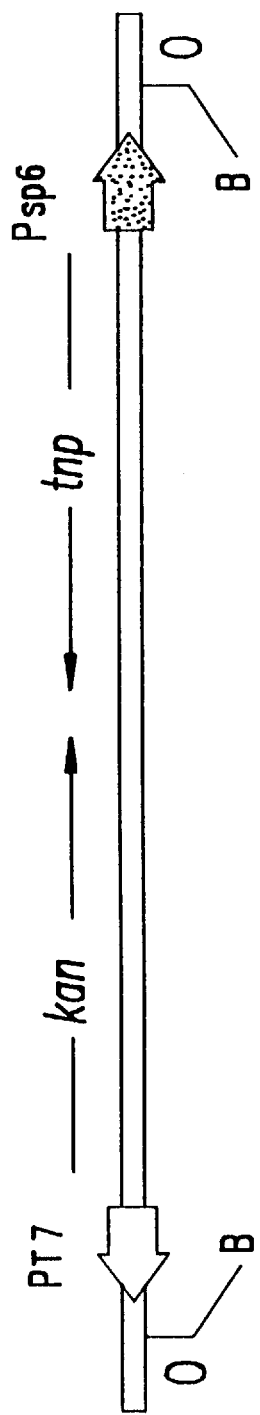

Plasmid pBRG1408 is on deposit at the American Type Culture Collection, Rockville, Md., under accession number ATCC 67513.

The construction of the plasmid pBR322-Tn5 derivative is described by Berg et al., *Genetics* 105, 813–828 (1983), the disclosure of which is incorporated herein by reference.

Standard biochemical nomenclature is used herein in which the nucleotide bases are designated as adenine (A); thymine (T); guanine (G); and cytosine (C). N connotates any of these nucleotides while Py refers to pyrimidine nucleotides and Pu refers to purine nucleotides. Corresponding nucleotides are, for example, deoxyadenosine-5'-triphosphate (dATP). As is conventional for convenience in the structural representation of a DNA nucleotide sequence, only one strand is usually shown in which A on one strand connotes T on its complement and G connotes C.

Commonly available restriction endonucleases used herein have the following restriction sequences and (indicated by arrows) cleavage patterns.

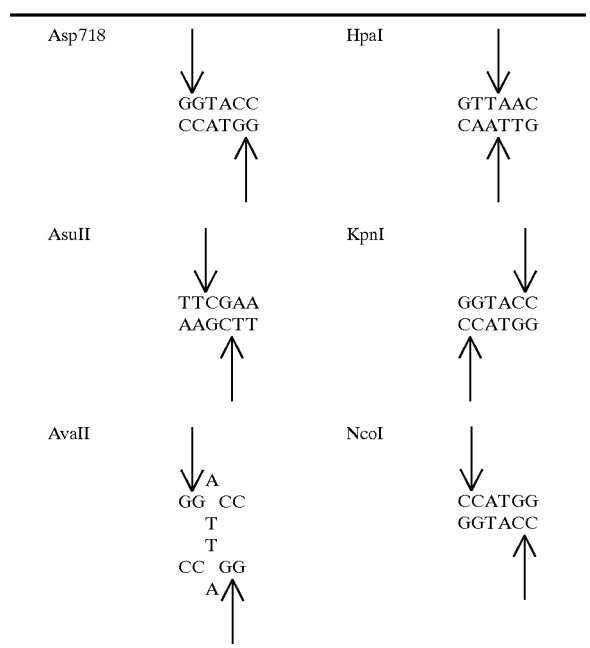

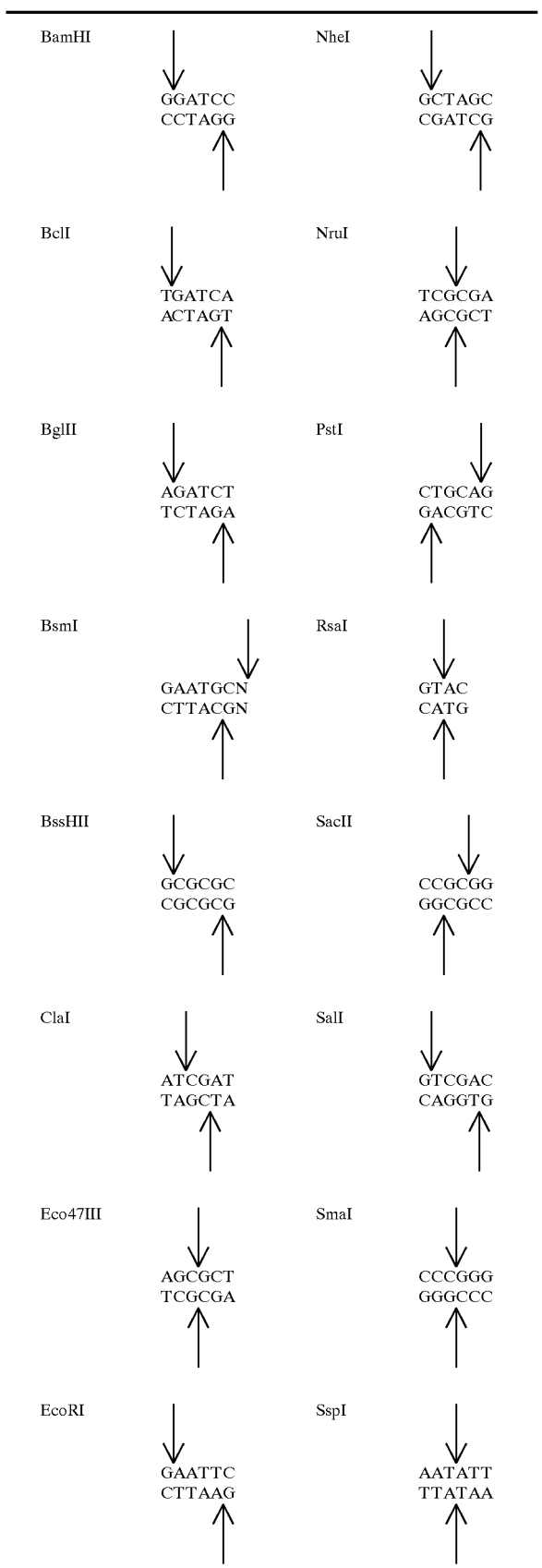

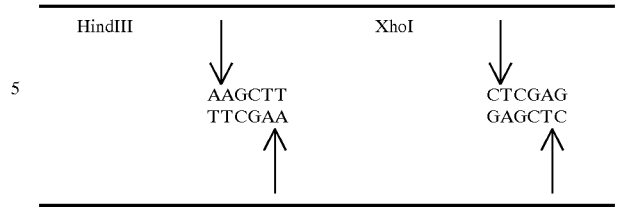

In order to illustrate specific preferred embodiments of the invention in further detail, the following exemplary laboratory preparative work was carried out.

Materials and Methods

Materials

2'-deoxy and 2'-3'-dideoxynucleotides were obtained from Pharmacia P-L Biochemicals. All radioactive materials were obtained from Amersham. Restriction endonucleases, T4 polynucleotide kinase, T4 DNA ligase, and the SP6 promoter primer (24-mer) were purchased from New England Biolabs, Inc. The T7 promoter oligonucleotide (20-mer) was obtained from Pharmacia. The Tn5 O end oligonucleotide was synthesized on an Applied Biosystems automatic oligonucleotide synthesizer. The sequences of the oligonucleotides are:

SP6 primer: 5' CATACGATTTAGGTGACACTATAG 3'
T7 promoter: 5' TAATACGACTCACTATAGGG 3'
3' ATTATGCTGAGTGATATCCC 5'
O-specific oligonucleotide:
5' GATCCTACTTGTGTATAAGAGTCAGGGTAC 3'

The underlined portion of the sequence is positioned at the right end of the transposon Tn5seq1. Only the top strand of the T7 promoter was used as a primer.

Bacteria, phages, and plasmids.

The bacteria, λ phages, and plasmids are described in Table 1, below. All bacterial strains are derivatives of *E. coli* K12.

Media

LN broth contains 10 g of Humko-Sheffield N-Z amine, 5 g of Difco yeast extract and 10 g of NaCl per liter adjusted to pH 7.2. LN agar contains 15 g of agar per liter of LN broth. Bottom agar used for λ plating contains 10 g tryptone, 5 g NaCl and 10 g agar per liter adjusted to pH 7.2. Top agar contains 10 g tryptone, 5 g NaCl, 2 g maltose, 10 mM $MgSO_4$ and 7 g agar per liter adjusted to pH 7.2. Antibiotics were used at the following concentrations: ampicillin 250 µg/ml, tetracycline 12.5 µg/ml, and kanamycin 50 µg/ml.

TABLE 1

| Bacterial strains, phages, and plasmids | |
|---|---|
| Bacterial strain, phage, or plasmid | Genotype |
| Bacteria | |
| MC1061 | F⁻ ara139 Δ(araCOIBA leu)7697 ΔlacX74 galU galK- r- m- |
| DB114 | F⁻ΔE5 hfl-1 supE |
| WM1100 | ΔrecA Tc$^r$ derivative of MC1061 |
| DB1221 | F⁻nusAl nusB5 spc$^r$ |
| DB973 | F⁻lac⁻trp⁻supF sm$^r$ |
| DB881 | F⁻$^{groP}$supE (λimm434 Pam80) |
| Phages | |
| λ b221 cI857 | |

TABLE 1-continued

Bacterial strains, phages, and plasmids

| Bacterial strain, phage, or plasmid | Genotype |
|---|---|
| λ b519 b515 cI857 xis6 nin5 Sam7 | |
| λ::b221 cI857 Pam80 | |
| Plasmids | |
| Proteus 23NB⁺ | Amp$^r$ with SP6 promoter upstream of a promoterless kan gene (2.975 kb) |
| Proteus 25 | proteus 23NB⁺ without the kan segment (2.166 kb). |
| pBRG1400 | Amp$^r$ and has IS50 transposase gene, O end sequences, and M13 Ori |
| pBRG1408 | Tn5seq1 containing plasmid. See FIG. 2 |
| pBRG1409 | Derived from pBRG1408 by digestion with BamHI and self ligation (1914 bp) |

Molecular Techniques

Plasmid DNA was prepared by the alkaline-SDS lysis procedure of Birnboim and Doly *Nucl. Acids Res.* 7, 1513–1523 (1979). Restriction digestion, ligation, and electrophoresis were performed as described in Maniatis et al., *Mol. Cloning; A Lab. Manual*, Cold Spring Harbor Lab., N.Y. (1982). Chromosomal DNA was prepared by a modification of the procedure in Silhavy et al., *Experiments with Gene Fusions*, Cold Spring Harbor Lab., N.Y. (1984). Specifically, the cells from 50 ml saturated LN broth cultures were collected by centrifugation and resuspended in 2.5 ml of 50 mM Tris-HCl, pH 8.0, 50 mM EDTA and frozen at −20° C. A fresh lysozyme soln (10 mg/ml in 0.25M Tris-HCl, pH 8.0) was prepared and 0.25 ml was added to the frozen cells. The cells were thawed at room temperature and then placed on ice for 45 min. One ml STEP soln (0.5% SDS, 50 mM Tris-HCl, pH 7.5, 0.4M EDTA and 1 mg/ml proteinase K) was added. The mixture was heated at 50° for one hr with occasional gentle stirring, followed by extraction twice with phenol and twice with chloroform:isoamyl alcohol (24:1). The DNA was precipitated with one-tenth volume of 3M sodium acetate and 2.5 volumes of ethanol, suspended in 3 ml of 50 mM Tris-HCl, pH 7.5, 1 mM EDTA, and 200 μg/ml of RNase A, incubated in a shaker water bath for three hours, extracted with phenol-chloroform, precipitated, washed, dried, and suspended in 300 μl of 10 mM Tris-HCl, pH 7.5, 1 mM EDTA.

Construction of Tn5seq1

Figure 2A:
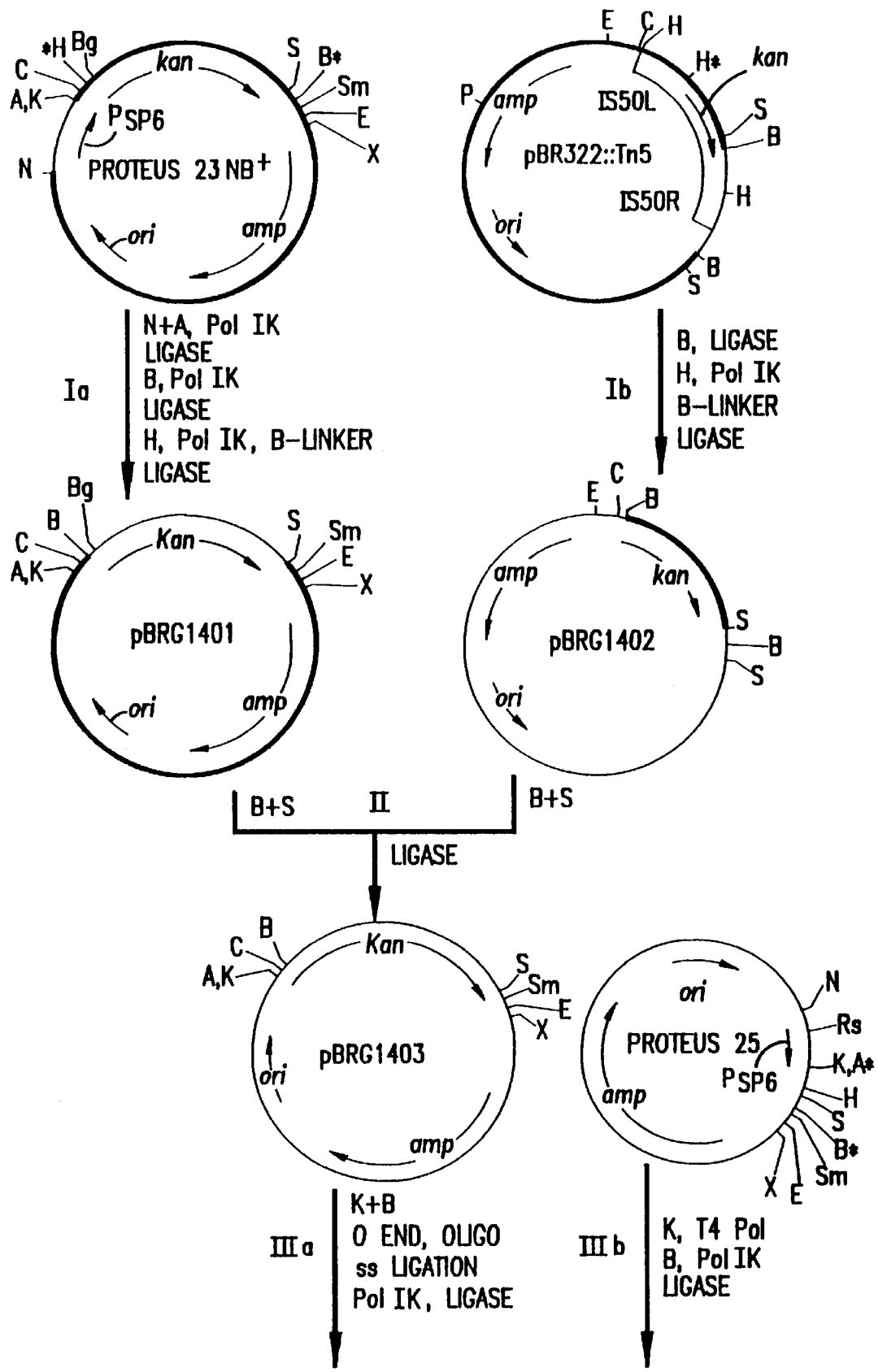
Figure 2B:
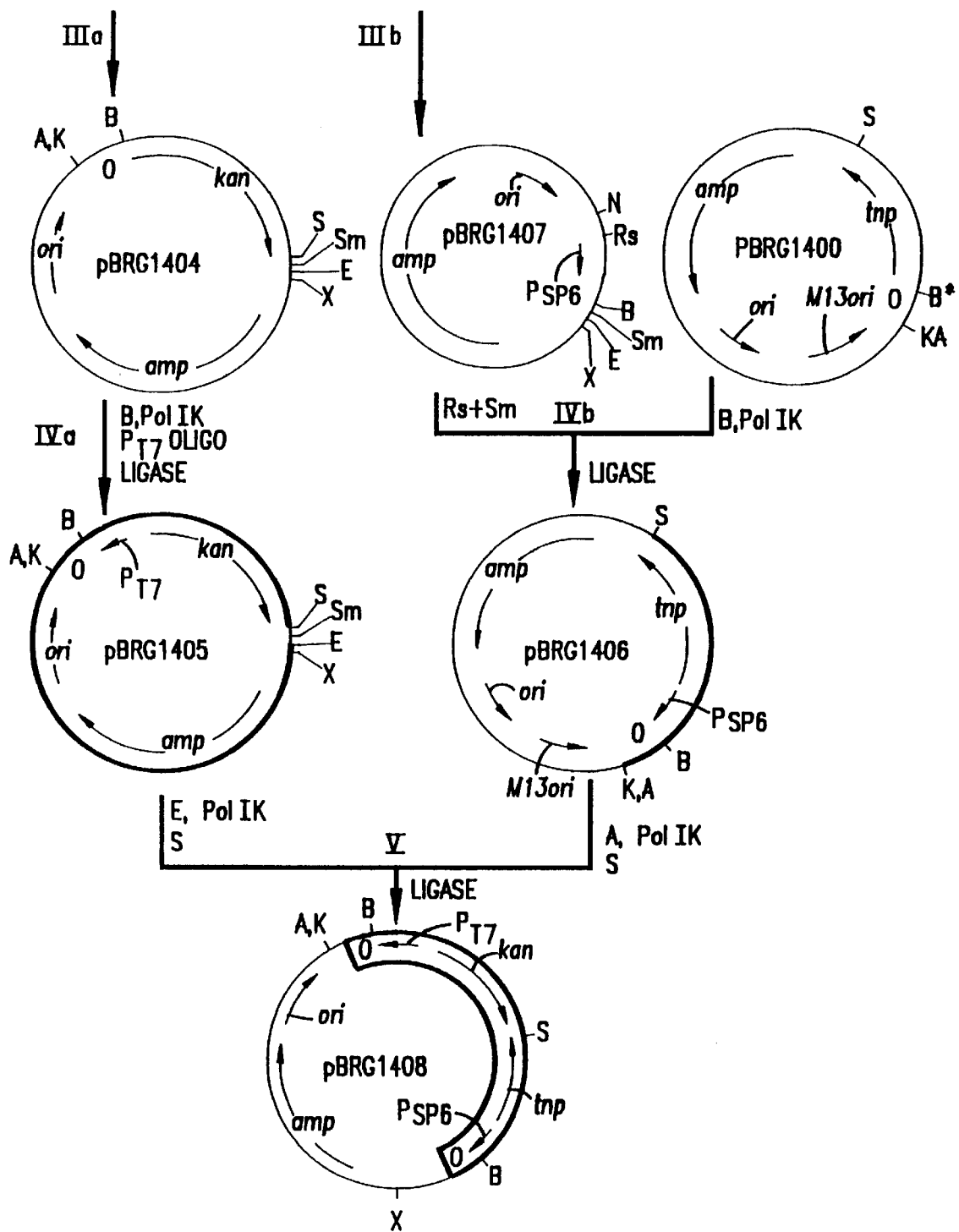
Figure 3:
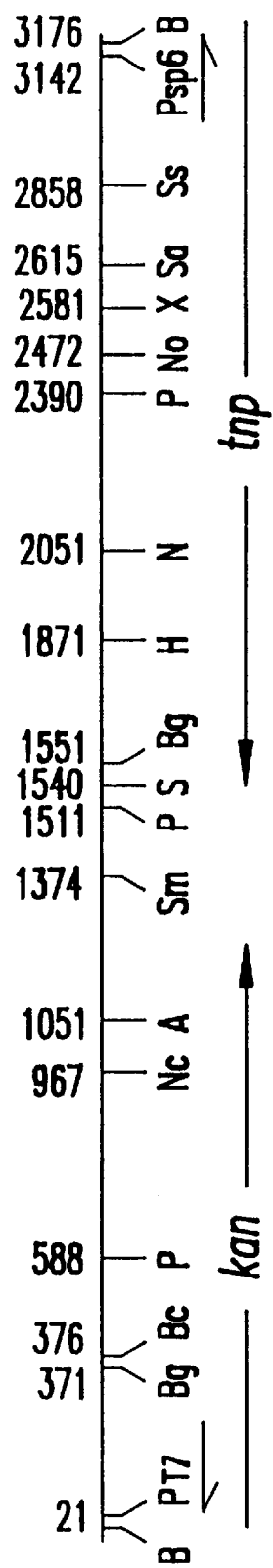
FIG. 3 shows the restriction enzyme map of Tn5seq1.

The Tn5seq1 transposon was constructed in a pBR322 derived plasmid as shown in FIG. 2 and described in detail below.

Construction of λ Carrying Tn5seq1

The λ phage vector used for transposition of Tn5seq1 to the *E. coli* chromosome and to plasmids is λ b221 cI857 Pam80. The 10.8 kb b221 deletion removes int and att which are necessary for λ prophage integration, but leaves genes essential for lytic growth. The selection of λ b221 carrying Tn5seq1 was based on the ability of such phages to persist as unstable Kan$^r$ plasmids in bacterial strains that interfere with λ N function (nus mutants, Friedman et al., *Microbiol. Rev.* 48, 299–325 (1984), and Berg, in *DNA Insertion Elements, Plasmids and Episomes*, Cold Spring Harbor Lab., N.Y., pp. 555–558 (1977). This block is leaky and colonies of Nus⁻ cells harboring λ plasmids also always contain some free phages. Phage λ b221 c1857 grown on MC1061 harboring pBRG1408 was used to infect the nusA⁻, nusB⁻ strain DB1221 at a multiplicity of 5–10 phages per cell. After adsorption, the infected cells were grown for two hrs at 30° and plated on kanamycin agar. Kan$^r$ colonies were screened for Amp$^s$ (absence of plasmid vector sequences) and the ability to form plaques when stabbed into a standard lawn of nus⁺ indicator bacteria. Phages obtained from Kan$^r$ Amp$^s$ colonies were purified, and a Pam80 allele was incorporated into a representative isolate to make it defective in replication (in su⁻ bacteria) as follows: a plate lysate of λ::Tn5seq1 b221 cI857 was prepared on the su⁺ strain DB973 made lysogenic for λimm434 Pam80 and the lysate was plated on the groP⁻ λimm434 Pam80 lysogen DB881, where only λ P⁻ phage can grow (Friedman et al., supra.) The plaques which appeared were tested for λ immunity and the ability to form plaques on an su⁺ but not an su⁻ host, and for the presence of the Kan$^r$ marker. Finally a stock lysate was prepared on DB973 for subsequent tests.

Isolation of Tn5seq1 insertions into plasmid

The recA⁻ su⁻ *E. coli* strain WM1100, harboring the target plasmid was infected with λ::Tn5seq1 at a multiplicity of five phages per cell. The cells were diluted with fresh medium and grown at 30° for two hrs to allow Tn5seq1 transposition and to express Kan$^r$, and then spread on kanamycin agar. Since any single Kan$^r$ colony on these plates could have Tn5seq1 inserted either in the plasmid or in the chromosome, plasmid DNA was isolated from a pool of the Kan$^r$ colonies and used to transform MC1061 to Kan$^r$. All Kan$^r$ transformants tested contained plasmids carrying Tn5seq1.

5' End-labeling of oligonucleotides for chromosomal sequencing

The T7 and SP6 primer oligonucleotides were kinased in 20 μl volume of 70 mM Tris-Cl, pH 7.6, 10 mM MgCl$_2$, 5 mM dithiothreitol (DTT), 16 pmoles of primer oligonucleotide, 4–5 units of T4 polynucleotide kinase and 12 μl of γ-[$^{32}$P]-ATP (specific activity 3000 Ci/mMole, 10 Ci/ml). The reaction was incubated at 37° for one hr, followed by inactivation of the enzyme at 65° for 10 min. Sequencing conditions:

1) Plasmid DNA

Double-stranded plasmid DNA sequencing was performed as described by Zagursky et al., *Gene Anal. Tech.* 2, 89–94 (1985). Plasmid DNA was isolated from a 5 ml overnight culture and the DNA was dissolved in 50 μl of water. 8 μl of this DNA was denatured with 0.2N NaOH and 0.2 mM EDTA, pH 8.0, in a total volume of 40 μl at room temperature for 5 min. One μl primer (1.25 pmoles) was added, which gave a molar ratio of template to primer of 1:5. Then the solution was neutralized by the addition of 4 μl of 2M ammonium acetate, pH 4.5, and the DNA was precipitated with 2 volumes of ethanol. The DNA pellet was rinsed with 70% ethanol, dried under vacuum, and resuspended in 11 μl water. Four μl buffer (0.3M Tris-HCl, pH 8.3, 0.375M NaCl, 37.5 mM MgCl$_2$, and 2.5 mM DTT), 1 μl AMV reverse transcriptase (20 units), and 4 μl [α-$^{32}$P]-dATP (specific activity 3000 Ci/mMole) were added. Four μl of this mixture was then added to each of four tubes labelled G, A, T, and C, each containing 1 μl of the corresponding dideoxy mixes, and incubated at 42° for 10 min (each of the dideoxy mixes contained 10 μM DATP, 60 μM dNTP of the corresponding ddNTP and 250 μM of the other two dNTPs; the A mixes contained 1.25 μM ddATP and the rest of the tubes contained 12.5 μM of the corresponding ddNTPs). Then 1 μl of chase solution (0.25 mM of four dNTPs) was added and the reactions were incubated for another 5 min at 42°. The reactions were stopped by the addition of 10 μl loading buffer (80% formamide, 10 mM NaOH, 1 mM EDTA, 0.1% xylene cyanole, and 0.1% bromophenol blue) and placed in a 95° water bath for 3 min. Four μl of this DNA was loaded on an 8% polyacrylamide gel. After electrophoresis, the gel was transferred onto an old film or Whatman 3 MM paper, covered with Saran wrap®, and exposed to Kodak XR5 film at −20° overnight.

2) Chromosomal DNA Sequencing

About 20 μg of PstI digested chromosomal DNA was denatured with 0.2N NaOH and 0.1 mM EDTA in a total volume of 40 μl for 5 min at room temperature. After the addition of 4 pmoles of 5' end labelled primer (molar ratio of template to primer of 1:500), the solution was neutralized with 4 μl of 2M ammonium acetate, pH 4.5. The primer-DNA mixture was precipitated with 2 vol of alcohol, washed, dried and finally dissolved in 15 μl water, and 4 μl of 5x Reaction Buffer (0.3M Tris-Cl, pH 8.3, 0.37M NaCl, 37.5 mM MgCl$_2$, and 2.5 mM DTT). The mixture was annealed at 42° for 15 min. The sequencing conditions were as described for plasmid sequencing, above, except that the film was exposed with an intensifier screen overnight at −70°.

The results of the above laboratory preparative work leading to the construction of the Tn5seq1 containing plasmid pBRG1408 and the use of this plasmid in bidirectional chain terminating DNA sequencing are further exemplified by the following detailed description of FIGS. 1 to 7 of the drawings.

FIG. 1

This figure shows the Tn5seq1 structure (not to scale). The positions and 5'→3' orientations of the T7 and SP6 primers (P$_{T7}$ and P$_{SP6}$) are represented by the solid and stippled arrows, respectively. Abbreviations used are: O, the first 19-bp from Tn5 ends; B, BamHI restriction sites; kan and tnp, genes encoding kanamycin resistance and transposase, respectively; P$_{T7}$ and P$_{SP6}$, primers recognized by RNA polymerases encoded by phages T7 and SP6, respectively.

FIG. 2

This figure shows the construction of the Tn5seq1 containing plasmid pBRG1408 (Plasmid and fragment sizes are not drawn to scale). The abbreviations for restriction sites used are: A, Asp718; B, BamHI; Bc, BclI; Bg, BglII; C, ClaI; E, EcoRI; K, KpnI; N, NheI; Rs, RsaI; S, SalI; Sm, SmaI; X, XhoI. PolIK is the Klenow fragment of DNA polymerase I. Only relevant restriction enzyme sites are shown. Asterisks indicate restriction sites inactivated during the construction. Bold lines indicate the fragments that are used in the next step of plasmid construction. The plasmid and DNA fragment sizes are not drawn to scale. The Tn5seq1 transposon in pBRG1408 is indicated by a box.

The detailed steps of Tn5seq1 construction follow. (Ia) The SP6 promoter present in Proteus 23NB+ was deleted by digesting the plasmid DNA with NheI and Asp718, followed by filling-in with polIK and self-ligation; this ligation regenerates another KpnI/Asp718 site. The BamHI site was inactivated with digestion with BamHI and filling-in with polIK; a BamHI linker (5' CGGATCCG) was introduced at the filled-in HindIII site to give pBRG1401. (IB) pBR322::Tn5 was digested with BamHI and self-ligated, then digested with HindIII, filled-in with polIK and ligated with a BamHI linker to yield pBRG1402. (II) The promoterless kan gene of pBRG1401 was replaced by the BamHI-SalI fragment from pBRG1402 containing the kan gene of Tn5 to give pBRG1403. (IIIa) One O end of IS50 was cloned into pBRG1403 by ligating a single stranded oligonucleotide containing the O end (see Materials, above) to plasmid pBRG1403 DNA between the BamHI and KpnI sites. The remaining gap was filled-in with polIK and ligated (Phadnis and Berg, *Proc. Natl. Acad. Sci. USA*, in press 1987) to yield pBRG1404. (IVa) The double-stranded T7 promoter oligonucleotide (see Materials, above) was cloned into the filled BamHI site of pBRG1404 to give pBRG1405.

The SP6 promoter was obtained from Proteus 25 by the following steps. (IIIb) Proteus 25 was digested with KpnI, and the single strand extension was removed by T4 DNA polymerase in the presence of all four dNTPs. It was then digested with BamHi, filled, and ligated to give pBRG1407. (IVb) Plasmid pBRG1407 was digested with RsaI and SmaI, and an 80 bp fragment containing the SP6 promoter was ligated into the filled-in BamHI site of pBRG1400 to give pBRG1406. (V) After filling the Asp718 and EcoRI sites of pBRG1406 the fragment was cloned into EcoRI-SalI digested pBRG1405 to give pBRG1408. Plasmid pBRG1408 carries the complete Tn5seq1 element. The constructions were verified at each step by tests of antibiotic resistance, plasmid size, restriction sites, or DNA sequencing, as appropriate.

FIG. 3

This figure shows the restriction map of Tn5seq1. Abbreviations for restriction sites used are B, BamHI; Bg, BglII; Bc, BclI; P, PstI; Nc, NcoI; A, AvaII; Sm, SmaI; S, SalI; H, HindIII; N, NheI; No, NotI; X, XhoI; Sa, SacII; Ss, SspI. P$_{T7}$ and P$_{SP6}$ indicate the position of promoter segments from phage T7 and SP6 to which the primer oligonucleotides are matched.

FIG. 4

This figure shows the complete nucleotide sequence of Tn5seq1, assembled from published component sequences [Auerswald et al., *Cold Spring Harbor Symp. Quant. Biol.* 45, 107–113 (1981); Beck et al., *Gene* 19, 327–336 (1982); and Mazodier, et al., *Nucl. Acids Res.* 13, 195–205 (1985)]. Unique restriction sites, transcriptional startpoints of T7 and SP6 polymerases, and the initiation and termination codons of tnp and kan genes are indicated. Tn5seq1 is not cleaved by the following restriction endonucleases: AatII, AflII, ApaI, ApaLI, AvrII, BspMII, BstEII, BstXI, ClaI, DraI, DraIII, EcoRI, EcoRV, EspI, HgiEII, KpnI, MluI, NdeI, NsiI, PflMI, PmaCI, PuMI, PssI, PvuI, SacI, SfiI, SnaI, SnaBI, SpeI, SplI, StuI, XbaI and XmnI.

FIG. 5

This figure shows Tn5seq1 facilitated double-stranded plasmid DNA sequencing. The DNA of a pBR322::Tn5seq1 plasmid was sequenced as described in Materials and Methods, above, with $^{32}$P-labelled SP6 and T7 primers (primer:template molar ratio=1:5). Samples were electrophoresed in an 8% polyacrylamide sequencing gel. After electrophoresis an Autoradiogram of the gel was prepared using Kodak XR5 film and overnight exposure at −20° C. The left panel shows the results using the SP6 primer; the right panel shows the results using the T7 primer. The sequences that are lettered correspond (from the bottom) to positions #9 to #1 of the Tn5seq1 O end, and then pBR322 positions #39 to #31 (left) and #31 to #39 (right).

FIG. 6

This figure shows Tn5seq1 facilitated genomic DNA sequencing. Total chromosomal DNA of *E. coli* lysogenic for λ::Tn5seq1 b519 b515 xis6 cI857 nin5 Sam7 was digested with PstI, denatured with alkali, and then annealed to the $^{32}$P-labelled T7 or SP6 primers. The primers were extended with AMV reverse transcriptase in the presence of chain terminators. Conditions for electrophoresis autoradiography were as in FIG. 5, except that the film was exposed with an intensifier screen overnight at −70° C. The left panel shows the results using the SP6 promoter primer; the right panel shows the results using the T7 promoter primer. The sequences that are lettered correspond (from the bottom) to positions #9 to #1 of the Tn5seq1 O end, and then λ positions #28142 to #28150 (left), and #28150 to #28142 (right).

FIG. 7

This figure shows agarose gel analysis of restriction endonuclease digestion of Tn5seq1 insertion derivatives of pBRG1409 that remained Amp$^r$. Lanes 1 and 12, HindIII digested λ DNA (size standards); lanes 2–11, BamHI digested plasmid DNAs; lane 2, pBRG1408; lane 11, pBRG1409; and lane 3–10, BamHI digested independent pBRG1409::Tn5seq1 transposition derivatives. The figure shows that Tn5seq1 can insert into many sites in a 368 bp segment and that the distribution of sites is not biased by remnant Tn5seq1 ends.

Tn5seq1 facilitated plasmid DNA Sequencing

Figure 5:
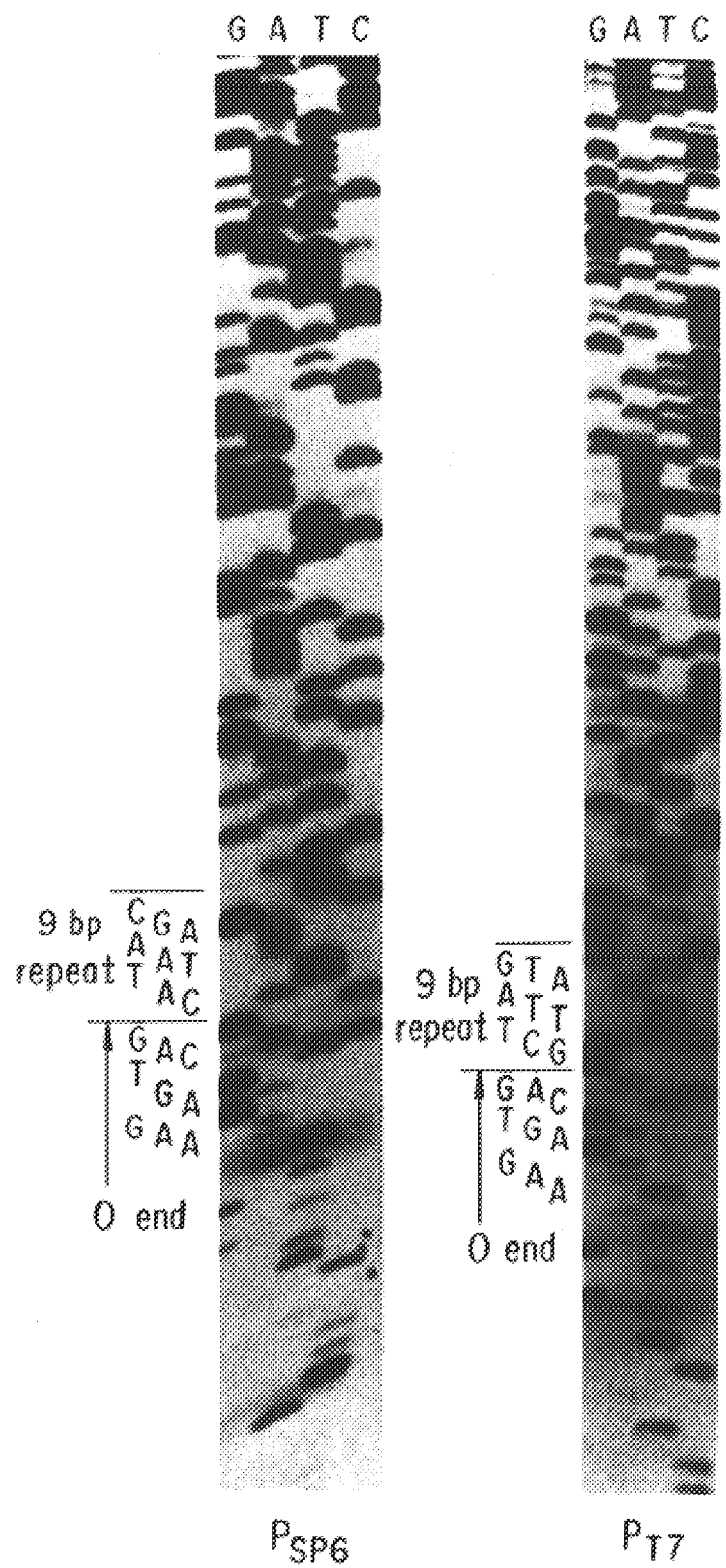
FIG. 5 shows the double-stranded DNA sequencing of Tn5seq1 containing plasmid DNA. The left Panel shows results with the SP6 primer; the right Panel shows results with the T7 primer.

To test the feasibility of Tn5seq1 for plasmid sequencing, it was transposed to plasmid pBR322. Strain WM1100 harboring pBR322 was infected with λ::Tn5seq1 (see methods, above) and Kan$^r$ colonies (formed by transposition) were obtained at a frequency of $10^{-4}$ per infected cell. Plasmid DNAs made from pool of the Kan$^r$ colonies were used to transform MC1061. Plasmids were isolated from representative Kan$^r$Amp$^r$Tet$^s$ and Kan$^r$Amp$^s$Tet$^r$ transformants, and several sites of Tn5seq1 insertion were determined. A representative sequencing result is shown in FIG. 5.

One fourth of all insertions of Tn5-wild type in the tet gene of pBR322 occur at position 31–39 (hotspot I) [Berg et al., *Bio/Technology* 1, 417–435 (1983)]. The restriction mapping and DNA sequence analysis showed that 2 of 12 Tn5seq1 insertions in the tet gene of pBR322 were also in hotspot I. This indicates that Tn5seq1 probably retains the insertion specificity of Tn5. The results in FIG. 5 and Table 2, below, indicate that Tn5seq1, like Tn5-wild type, makes nine bp target sequence duplications.

It was concluded that Tn5seq1 is useful for the sequencing of genes cloned in multicopy plasmids. The unique sequences near each end permit sequencing in both directions from a single site of insertion.

TABLE 2

DNA sequence analysis of Tn5seq1 indertions in pBR322 and λ.

| Insertion in | Position of insertion[a] | Target sequence duplicated[b] |
|---|---|---|
| pBR322 | 31 to 39 | 5' GCTTTAATG 3' |
| pBR322 | 149 to 157 | GGCTTGGTT |
| pBR322 | 303 to 311 | GCCCAGTCC |
| Lambda | 28,142 to 28,150 | ATGCAATGC |
| Lambda | 23,046 to 23,054 | GATTAAATC |

[a]pBR322 and λ coordinates are as in Maniatis et al., supra. and Daniels et al. in Hendrix et al., Lambda II. Cold Spring Harbor Lab., N.Y. (1983), respectively.
[b]Nine bp sequences duplicated by insertion are indicated.

Chromosome Sequencing

Figure 6:
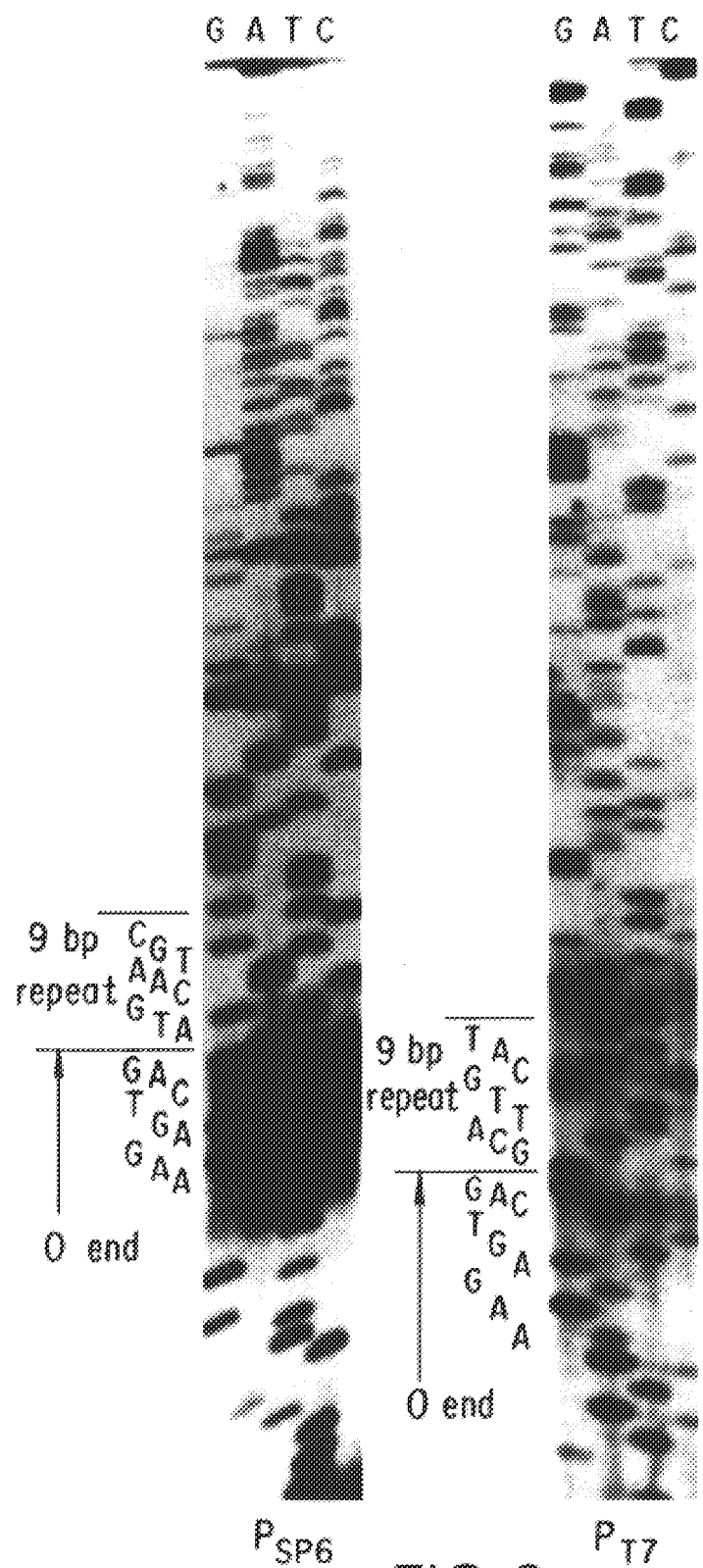
FIG. 6 shows the double-stranded DNA sequencing of Tn5seq1 containing total chromosomal DNA. The left Panel shows results with the SP6 primer; the right Panel shows results with the T7 primer.

To assess the feasibility and accuracy of bacterial genomic sequencing, a Tn5seq1 at a chromosomal site of known sequence was required. To avoid the selection and screening that would have been needed to get Tn5seq1 into an already sequenced chromosomal site Tn5seq1 was transposed to the integration proficient phage λ b515 b519 cI857 xis6 nin5 Sam7 and this λ::Tn5seq1 phage was used to lysogenize *E. coli* strain DB114. The sequence of the entire λ genome is known, and since λ DNA becomes part of the host chromosome in the lysogenic state, sequencing from sites of Tn5seq1 insertion in a λ prophage is equivalent to sequencing from any other chromosomal Tn5seq1 insertion. Total genomic DNA isolated from cultures of λ::Tn5seq1 lysogen were digested with the restriction enzyme PstI, which does not cleave within or near the 3' ends of the primer sites, and then sequenced in the standard protocol using 5' end-labelled SP6 and T7 promoter primers. Representative results are shown in FIG. 6. The sequence obtained matches perfectly with known lambda sequences.

Both DNA polymerase I Klenow fragment and AMV reverse transcriptase have been tested; optimal results (lowest background) were obtained with reverse transcriptase at 42°.

Repeated transposition and sequencing

Once Tn5seq1 is inserted in a particular gene in the chromosome, the mutant gene can be easily cloned using the Kan$^r$ marker. After initial sequencing using Tn5seq1, the sequence of the rest of the cloned segment can be determined by removing Tn5seq1 and then generating new insertions of Tn5seq1 in the cloned segment. The internal region of Tn5seq1 including the primer sites can be removed using the two BamHI sites near each end of the transposon (FIG. 2). BamHI digestion and ligation leaves two O end sequences, a total of 55 bp, in the cloned segment. To determine if the remnant O ends behave as a hotspot for Tn5seq1 insertion, perhaps due to sequence homology, the Tn5seq1 containing plasmid pBRG1408 was digested with BamHI, to give pBRG1409, which retains just the two O end sequences from Tn5seq1 and then used it as a target for Tn5seq1 transposition. Among 155 insertions of Tn5seq1 into pBRG1409, 113 were in the amp gene and 42 were found outside the amp gene. Since the plasmid pBRG1409 is 1914 bp long, and contains an amp gene of 932 bp and 368 bp nonessential sequences in addition to the replication origin region, the distribution of insertions correlates well with the lengths of the corresponding segments in the plasmid.

Figure 7:
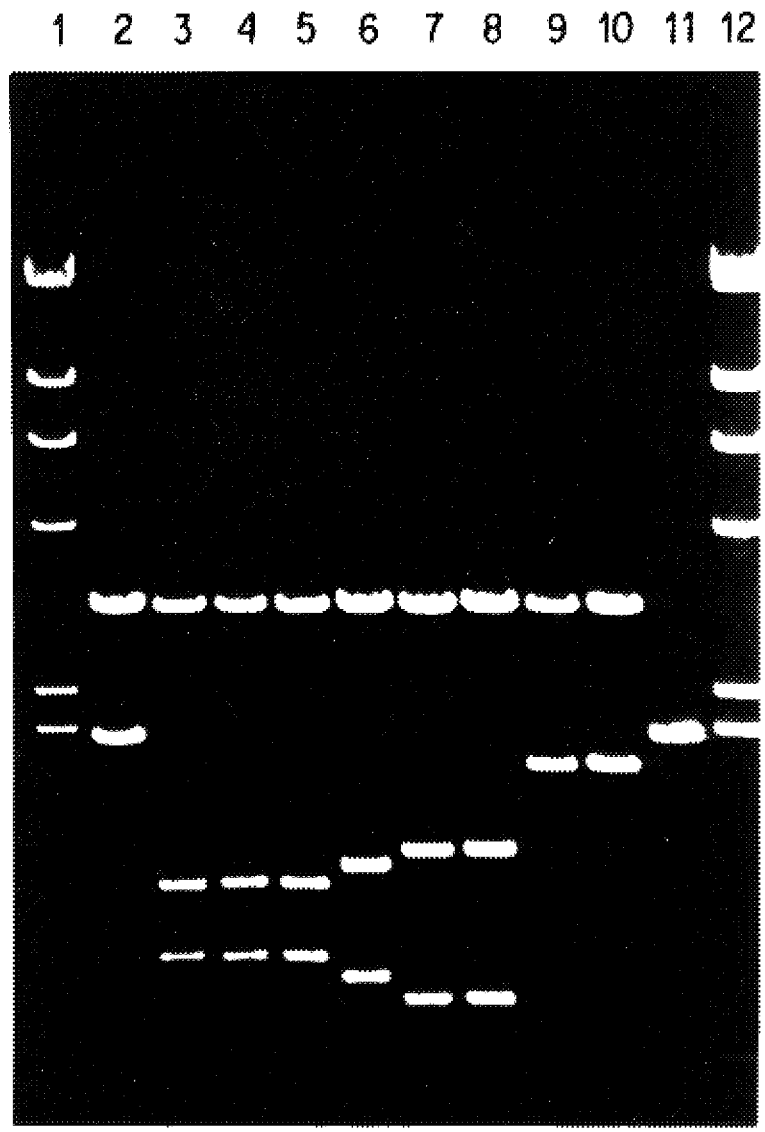
FIG. 7 shows agarose gel analysis of restriction endonuclease digestion of Tn5seq1 insertion derivatives of pBRG1409 that remained Amp$^r$.

The proximity of Tn5seq1 insertions to the remnant O ends in pBRG1409 were determined by restriction digestion. Because of the BamHI site between the remnant O ends, digestion of pBRG1409 with BamHI generates one fragment of 1914 bp. BamHI digestion of pBRG1409::Tn5seq1 generates three fragments due to additional two BamHI sites in Tn5seq1. A fragment of about 1900 bp is expected if the insertion is within or near the remnant O end sequences. At least four different sites of insertion were found. None of 12 Tn5seq1 insertion derivatives of pBRG1409 that were Amp$^r$ and thus contained the insert in the 368 bp non-essential region exhibited a BamHI fragment of about 1900 bp (FIG. 7). This indicates that the presence of the two O end sequences does not create a major hotspot for Tn5-seq1 insertion.

Various other examples will be apparent to the person skilled in the art after reading the disclosure herein without departing from the spirit and scope of the invention. It is intended that all such other examples be included within the scope of the appended claims.

What is claimed is:

1. A method of RNA transcription comprising inserting into a DNA molecule of an *E. coli* cell to obtain hyperexpression of genes adjacent to strong promoters SP6 or T7 a transposon Tn5seq1 having the nucleotide sequence shown in FIGS. 4A and 4B.

2. The method of claim 1 in which transposon Tn5seq1 is carried in plasmid pBRG1408.

* * * * *